(12) United States Patent
Meunier et al.

(10) Patent No.: US 8,372,997 B2
(45) Date of Patent: Feb. 12, 2013

(54) PROCESS AND DEVICE FOR MANUFACTURING ORGANOMETALLIC COMPLEXES IN POWDER FORM

(75) Inventors: Jean-Philippe Meunier, Cessy (FR); Sébastien Oguey, Reverolle (CH)

(73) Assignee: Pancosma Societe Anonyme pour l'Industrie des Produits Biochimiques, Le Grand-Saconnex (CH)

( * ) Notice: Subject to any disclaimer, the term of this patent is extended or adjusted under 35 U.S.C. 154(b) by 660 days.

(21) Appl. No.: 12/542,342

(22) Filed: Aug. 17, 2009

(65) Prior Publication Data

US 2010/0056817 A1  Mar. 4, 2010

(30) Foreign Application Priority Data

Aug. 26, 2008  (FR) ...................... 08 55713

(51) Int. Cl.
| | |
|---|---|
| C07F 1/00 | (2006.01) |
| C07F 3/00 | (2006.01) |
| C07F 15/00 | (2006.01) |
| F27B 15/00 | (2006.01) |
| B29B 9/00 | (2006.01) |

(52) U.S. Cl. ............ 556/112; 556/121; 556/140; 425/7; 422/140; 422/144; 264/12

(58) Field of Classification Search .................. 556/112, 556/121, 140; 425/7; 264/12; 422/144, 422/140
See application file for complete search history.

(56) References Cited

U.S. PATENT DOCUMENTS

| | | | | |
|---|---|---|---|---|
| 4,111,853 A | * | 9/1978 | Shultz et al. .................. 510/536 |
| 5,213,838 A | * | 5/1993 | Sheikh .......................... 426/649 |
| 5,468,720 A | * | 11/1995 | Lisa et al. ..................... 504/236 |
| 5,840,358 A | * | 11/1998 | Hofler et al. .................. 426/467 |
| 2006/0228661 A1 | | 10/2006 | Jacob | |

FOREIGN PATENT DOCUMENTS

| | | |
|---|---|---|
| EP | 0256645 A2 | 2/1988 |
| WO | 03/049850 A2 | 6/2003 |
| WO | WO 03/049850 A2 * | 6/2003 |

OTHER PUBLICATIONS

Nakamura et al., Journal of the Ceramic Society of Japan, vol. 111, No. 2, pp. 142-146 (2003).*

* cited by examiner

*Primary Examiner* — Porfirio Nazario Gonzalez
(74) *Attorney, Agent, or Firm* — William H. Eilberg (57) ABSTRACT

According to the invention, powders of low hygroscopicity are prepared by granulation of an aqueous solution (1) in a fluidized bed (140). A compound formed from crystalline grains whose moisture content is defined and stable is obtained. The invention applies especially to organometallic complexes of glycine with a metal.

14 Claims, 4 Drawing Sheets

PROCESS AND DEVICE FOR MANUFACTURING ORGANOMETALLIC COMPLEXES IN POWDER FORM

TECHNICAL FIELD OF THE INVENTION

The invention relates to organometallic complexes conditioned in powder form, which, by virtue of their nature, are intended to be used as a bioavailable metal source for man or animals. These complexes are generally combinations of amino acids and metals, and are referred to by the names chelates or complexes.

When exposed to moist air, such complexes in powder form are liable to rapidly take up moisture. Conversely, when exposed to temperature rises, they are liable to lose water. In so doing, they become hard, set to a solid, form a crust, or even become pasty or liquid. This phenomenon is known as caking or deliquescence. As a result, the complexes are then no longer water-soluble and simultaneously fully dispersible.

These drawbacks greatly hamper the essential uses of these complexes for animal feed, in which it is desired to be able to uniformly mix a small dose of the complex into a substrate, for example in a dose from about 1 to 1000 grams per ton, or into mixtures in a dose from about 1 to 250%.

Specifically, a sufficiently fine powder, whose fineness remains sufficient during mixing with the substrate, is required. However, under the usual conditions of the use, the substrate often contains a certain amount of free water. Mixing is then possible only if the hygroscopicity of the powder is low enough for its grains to remain detached and dispersible despite the presence of moisture.

The invention relates in particular to organometallic complexes of water-soluble amino acids such as glycine, valine, threonine, lysine, etc.

At the present time, a limited number of techniques are used for obtaining products in powder form, the most common of which is spray-drying.

Spray-drying consists in introducing the concentrated aqueous solution containing the product to be dried into a turbomixer or nozzles so as to spray this solution as fine droplets in a chamber at high temperature (between 150 and 220° C.). The water is immediately evaporated therein, and the very fine product particles are transported by a stream of air into a cyclone to separate the moist air and the dry product.

The spray-drying technique necessarily produces amorphous sprayed droplets of very small size, with a very low water content. It does not enable efficient selection of the moisture content and the particle size of the finished product. The product obtained is of very high hygroscopicity, which leads to caking or deliquescence phenomena.

The invention is directed toward solving this problem by giving the complex a suitable physical and/or chemical form that inherently has a markedly lower hygroscopicity than similar compounds obtained by means of the processes usually used, without harming the water-soluble nature. In practice, the invention proposes a crystalline organometallic complex in which the amino acid is bonded to the metal via at least one oxygen of its carbonyl group.

To produce zinc, copper, iron or manganese glycinates as a crystalline powder, document WO 2003/049 850 has recently recommended the use of vacuum drying with blending in a vacuum-drying installation, while dissuading the use of any other technique (atomization, fluidized bed, etc.). Specifically, it appears possible to produce crystalline powders, while controlling, via this technique, the drying time. However, the experiment showed that vacuum drying presents several drawbacks:

the manufacturing time for a batch is long, leading to high costs;

the use of very large dryers does not afford a consequential gain in productivity;

the manufacturing process is very sensitive, and the slightest change in one of the drying parameters (temperature, pressure, stirring, etc.) leads to a change in the quality of the finished product and changes the drying time;

the manufacturing process requires high technical competence to enable maintenance of a consistent quality.

As a result, the quality of the powders obtained industrially by such a process is not consistent and reproducible.

SUMMARY OF THE INVENTION

The problem proposed by the present invention is that of avoiding the drawbacks of the known processes, by proposing a novel process for producing organometallic complexes of amino acid that are water-soluble and fully dispersible, and that show great stability under the usual conditions of use.

It is particularly sought for the process to give a sufficiently consistent and reproducible result.

The invention is directed toward solving this problem without adding additional products.

The idea that forms the basis of the invention is that of using the fluidized bed technique, contrary to the dissuasion expressed in document WO 2003/049 850, and of adapting means for controlling the granulation and crystallization of the organometallic complex.

To achieve these aims and others, the invention especially proposes a process for producing a crystalline organometallic complex in powder form, comprising steps of:

a) preparing an aqueous solution of the organometallic complex, b) granulating and drying said solution by spraying in a fluidized bed by circulation of air, c) extracting the powder grains from the fluidized bed when they have reached a size greater than a predetermined lower size limit and a moisture content below a predetermined maximum moisture content.

The stability properties of the powders obtained then depend essentially on their particle size at the end of the process, the moisture content possibly varying within quite large proportions, i.e. from 2% to 20% by weight, without this harming the stability.

The granulation process may be performed by a system operating in batchwise (discontinuous) or continuous manner. For these two systems a certain number of parameters must be mastered in order to obtain a final product whose properties are consistent.

As a priority, it is important to obtain a satisfactory size.

According to one possibility, said predetermined lower size limit is about 25 μm. This makes it possible to obtain satisfactory stability with respect to ambient hygrometry, and adaptation to applications such as aquaculture and the feeding of pets or companion animals.

According to another possibility, said lower size limit is about 80 μm. This makes it possible to obtain satisfactory stability with respect to ambient hygrometry in applications for the feeding of reared animals such as cattle.

Preferably, the size of the grains is between a predetermined lower size limit and a predetermined upper size limit. Better homogeneity of the batches produced and of their properties is thus promoted, and the presence of grains that are too large for applications in animal feed is avoided.

In practice, during the step of granulation and drying in a fluidized bed, the temperature and flow parameters of the aqueous solution and of the air are chosen so as to obtain, at the end of the step, powder grains having a predetermined moisture content.

To do this, the flow rate (kg/minute) of the aqueous solution to be dried is determined from the air inlet and outlet temperatures, so as to manufacture a product having a predetermined moisture content and a desired physical and chemical structure.

The predetermined maximum moisture content may advantageously be between 2% and 20% by weight.

According to a first embodiment, the process is continuous. In this case:
- said solution is granulated and dried continuously by spraying in an air-fluidized bed,
- the temperature and flow parameters of the aqueous solution and of the air are continuously adapted so as to obtain in the fluidized bed a moisture content below a predetermined maximum moisture content,
- the powder grains having a size greater than a predetermined lower size limit are continuously extracted from the fluidized bed.

During a preliminary training step, inlet air, outlet air and inlet aqueous solution flow rates and temperatures may be determined, these flow rates and temperatures making it possible to produce a flow of outlet powder grains having a chosen moisture content, measured by collecting samples, that is lower than the maximum predetermined moisture content. It then suffices to maintain said flow rate and temperature values throughout the process, in order to obtain, at the outlet, powders having the desired physical and chemical structure, and the desired properties.

According to a second embodiment, the process is performed in batch mode, and one mass of material is processed in a single batch. In this case:
- a batch of material is granulated and dried by spraying said solution in a fluidized-air bed,
- after the powder grains in the fluidized bed have reached a size larger than the predetermined lower size limit, the spraying is stopped while continuing maintenance in the fluidized bed to perform drying until a moisture content below the predetermined maximum moisture content is reached,
- the mass of powder grains having this size and this moisture content is extracted.

The first step of the process, according to which an aqueous solution of the organometallic complex is prepared, allows production of the complex itself, via a complexation reaction.

To do this, during this step, a mixture temperature in the range from 55° C. to 80° C. may advantageously be maintained.

Preferably, during this step of preparing the aqueous solution of the organometallic complex, water, amino acid and a water-soluble metal salt may be mixed together with heating, in a mixer, until a temperature of 80° C. is reached, this temperature being maintained for a duration, greater than 15 minutes, that is sufficient for the complexation reaction.

In practice, it is preferable to introduce the water and to heat it first, in the mixer, and then to add the amino acid and the metal salt in an equimolar amount, and the mixture is stirred and heated until a temperature from 55° C. to 80° C., preferably 80° C., is reached, for at least 15 minutes depending on the metal under consideration.

According to a first application of the process, to prepare anhydrous iron glycinate, glycine is used as amino acid, iron II sulfate heptahydrate is used as metal salt, and the moisture content is about 6%.

According to a second application, to prepare copper glycinate dihydrate, glycine is used as amino acid, copper sulfate pentahydrate is used as metal salt, and the moisture content is about 13%.

According to another application, to prepare anhydrous zinc glycinate, glycine is used as amino acid, zinc sulfate monohydrate is used as metal salt, and the moisture content is about 2%.

According to another application, to prepare zinc glycinate dihydrate, glycine is used as amino acid, zinc sulfate monohydrate is used as metal salt, and the moisture content is about 13%.

According to another application, to prepare zinc glycinate trihydrate, glycine is used as amino acid, zinc sulfate monohydrate is used as metal salt, and the moisture content is about 17%.

According to another aspect, the invention proposes a device for implementing the process as defined above, the device comprising:
- a mixer and heating and temperature regulation means for producing a homogeneous aqueous solution of organometallic complex at a suitable temperature,
- a fluidized-bed spraying system, with a cavity and means for creating an ascending flow of suspending air in the cavity, and with means for receiving from the mixer a suitable flow of said aqueous solution of organometallic complex and for spraying it in the cavity,
- extraction means for extracting from the fluidized bed the powder grains having a satisfactory size and a satisfactory moisture content.

Preferably, the extraction means comprise a selection device for collecting powder grains in the fluidized bed, means for selecting and removing at the outlet, among the collected powder grains, those that have a satisfactory size, and means for recycling into the fluidized bed the unselected powder grains.

BRIEF DESCRIPTION OF THE DRAWINGS

Other subjects, characteristics and advantages of the present invention will emerge from the following description of particular embodiments, which is given in relation with the attached figures, among which.

DESCRIPTION OF THE PREFERRED EMBODIMENTS

Figure 1:
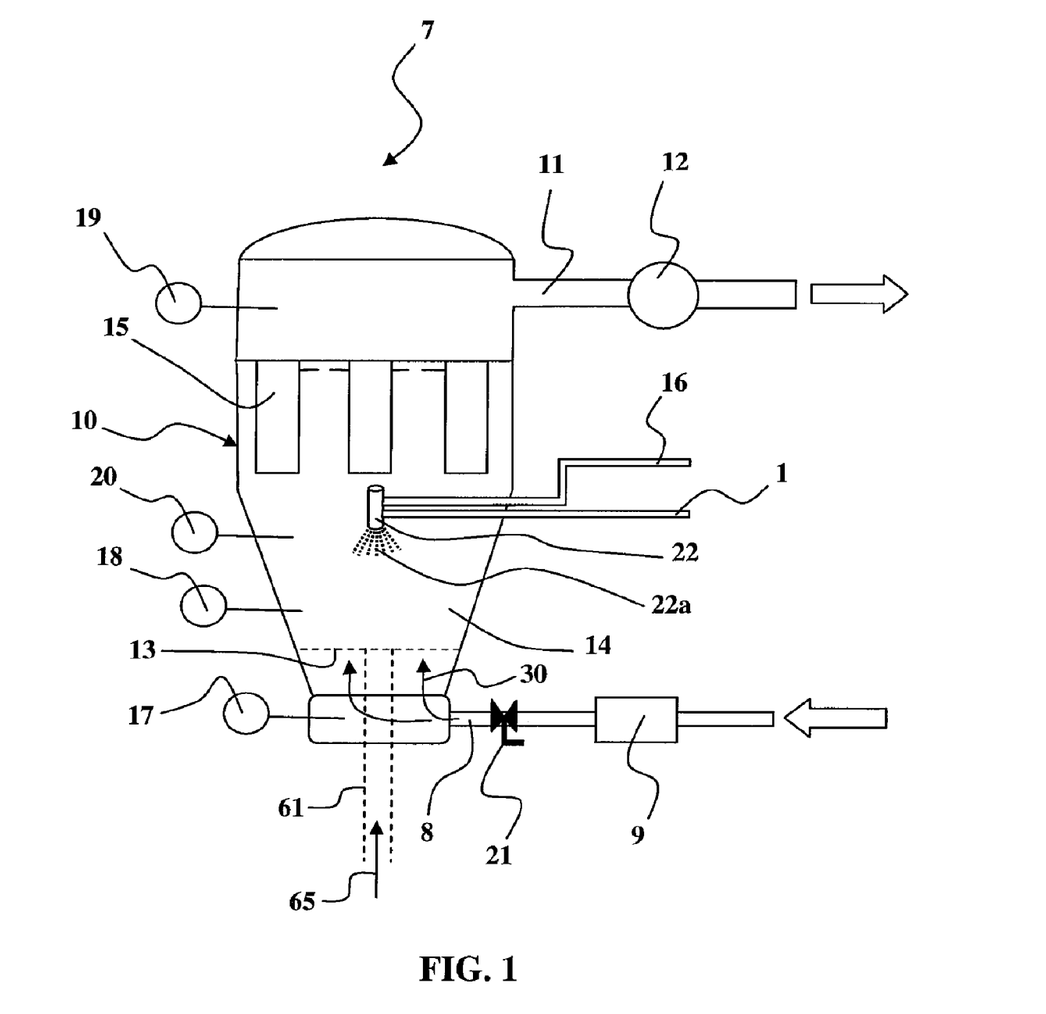
FIG. 1 is a schematic view of a fluidized-bed granulation installation, according to a batchwise or continuous treatment process.
Figure 2:
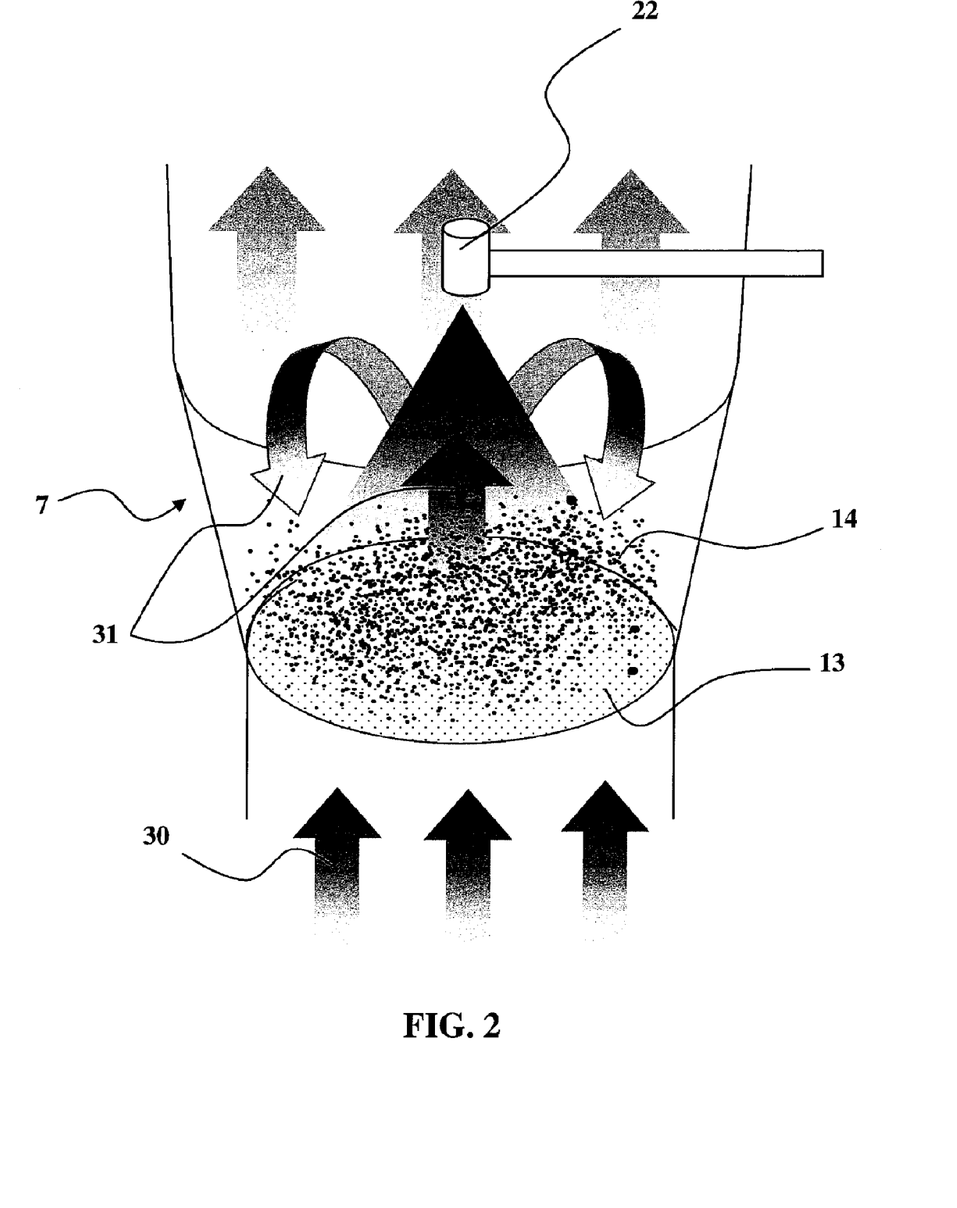
FIG. 2 schematically illustrates the functioning of a top-injection fluidized bed.
Figure 3:
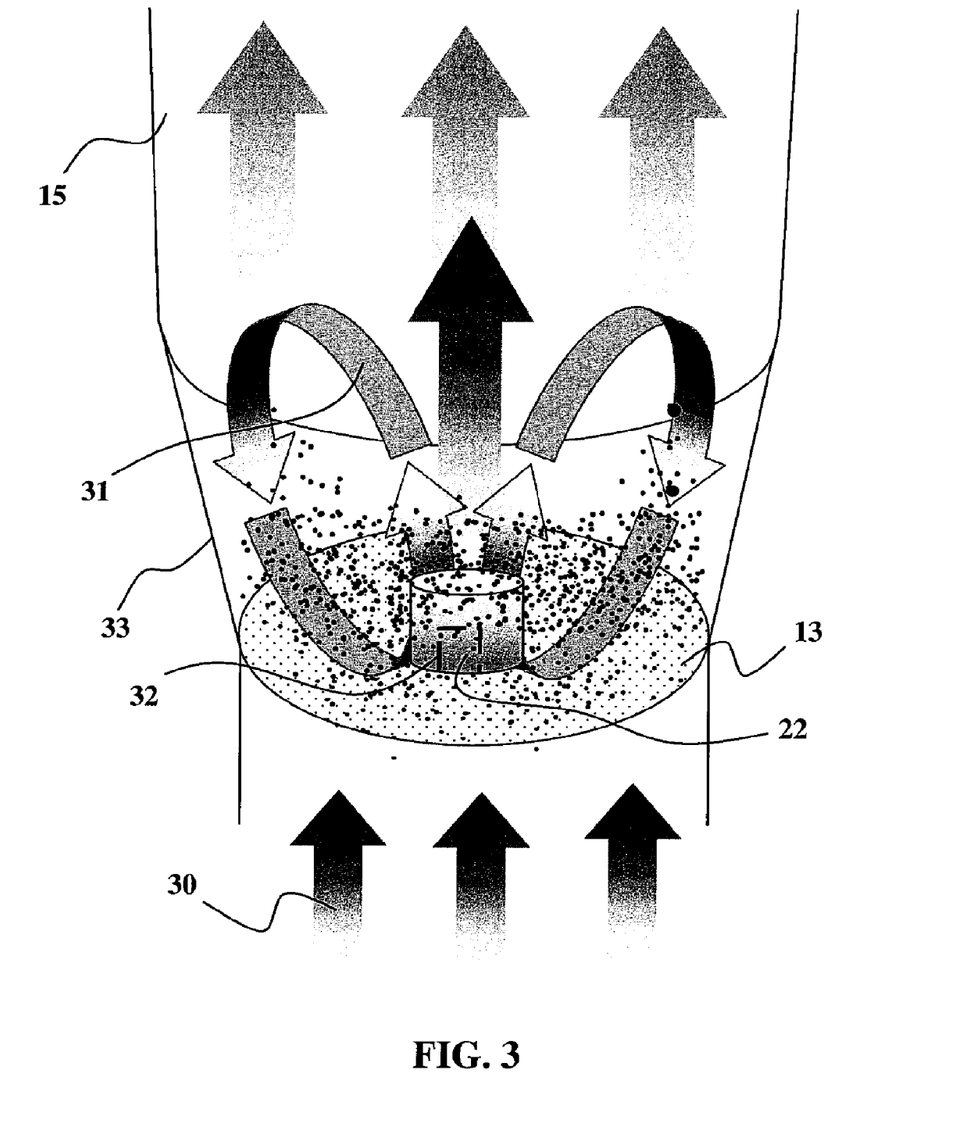
FIG. 3 schematically illustrates the functioning of a bottom-injection fluidized bed.

Reference is now made to FIGS. 1, 2 and 3 for the explanation of the fluidized bed technique.

The principle of the fluidized bed is based on the creation of a flow of ascending suspending air via a suction phenomenon. This ascending air flow, whose pressure and temperature are set according to predefined parameters, is channeled so as to pass from the bottom upward through a bed of pulverulent material and place it in suspension.

The following may be seen in the fluidized-bed system 7 according to FIG. 1: a suspending-air inlet 8 with a filtering and heating system 9, allowing hot suspending air 30 to enter at the base of a cavity 10 having an upper air outlet 11 connected to the atmosphere via a suction device 12. A distribution grille 13, in the lower area of the cavity 10, limits the base of a fluidized-bed area 14, or area for spraying onto pulverulent products. Above the fluidized-bed area 14 is a filtering area 15, upstream of the outlet 11 in the direction of flow of the suspending air.

Liquid spraying means are provided in the device to spray the aqueous solution of organometallic complex in the fluidized-bed area 14. In the embodiment illustrated in FIG. 1, spraying is performed from the top (top spraying). The spraying is performed by injecting the aqueous solution 1 and spraying air 16.

The suspending-air 30 inlet temperature is controlled via lower temperature control means 17, the temperature in the fluidized-bed area 14 is controlled via intermediate temperature control means 18, the air outlet 11 temperature is controlled via upper temperature control means 19, and the moisture content in the powder grains in the fluidized-bed area 14 is controlled via a moisture control device 20. The amount of suspending air 30 admitted is controlled via an air inlet valve 21.

The spraying nozzle 22 is placed above the particles suspended in the fluidized-bed area 14, and the spraying 22a of the wetting agent is performed from the top downward.

Starting from the bottom of the cavity 10 limited by the grille 13, the particles are entrained and accelerated by the suspending-air stream 30, pass close to the spraying nozzle 22 and receive droplets of the aqueous solution of organometallic complex emerging therefrom. The droplets of aqueous solution become deposited on the particles, forming a coating layer each time they pass. This operation is performed counter-currentwise relative to the flow of the product. The particles undergo an ascending motion crossing the fluidized-bed area 14 toward the upper part or expansion chamber of the cavity 10. They are then slowed down when they reach the top of the expansion part, and then fall back down on the sides and are again subjected to the fluidizing air stream. This cycle continues throughout the process.

The apparatus is thus composed of two sections in contact with the product:
  a cavity 10 advantageously in the form of a conical tank, equipped with a perforated base or grille 13 for retaining the product to be treated, and equipped with the spraying nozzle 22 oriented downward, which can be positioned in two levels of the tank according to the amount of product treated;
  an upper extension that forms the housing of a sleeve filter, constituting the filtering area 15 for retaining the product undergoing processing to prevent it from escaping via the upper air outlet 11.

Periodically, during the process, the filter is unclogged by mechanical shaking, which allows the fine particles to return into the fluidized bed in order to continue the granulation.

FIG. 2 once again illustrates, in partial perspective, the system 7 of FIG. 1, by representing the flow of ascending suspending air 30 and the flow of the particles 31 in the fluidized-bed area 14.

FIG. 3 illustrates a bottom-spraying fluidized-bed granulation system. The spraying nozzle 22 is placed at the bottom of the tank, at the center of the perforated plate or grille 13, and a cylinder 32 is mounted thereon. Spraying of the aqueous solution of organometallic complex is performed from the bottom upward. The apparatus is composed of a conical-shaped removable tank 33 of Würster type that fits onto the housing of the sleeve filter 15 of the apparatus. The tank 33 comprises a perforated tank bottom plate 13, a cylinder 32 (optional) located in the lower part of the tank above the perforated plate, and the height of which is adjustable, and a nozzle 22 located at the center of the perforated plate 13, under the cylinder 32, and oriented for spraying from the bottom upward. The larger volume of air that pass through the center of the perforated plate 13 and the inner cylinder 32 thereby create an ascending flow 31 of material, which then redescends outward, giving the particles in suspension a "fountain" motion. The suspended material circulates rapidly in this manner and, at each passage of the product close to the spraying nozzle 22, receives an additional layer of liquid coating. Stopping of the spraying of the coating liquid is followed by drying, which takes place in the same tank, by simply increasing the temperature and the flow rate of the entering ascending air 30. Grains of material with a very uniform surface are thus obtained.

A fluidized-bed process in continuous mode, rather than in batch mode, may advantageously be used. Examples are illustrated schematically in FIGS. 4 and 5.

Figure 4:
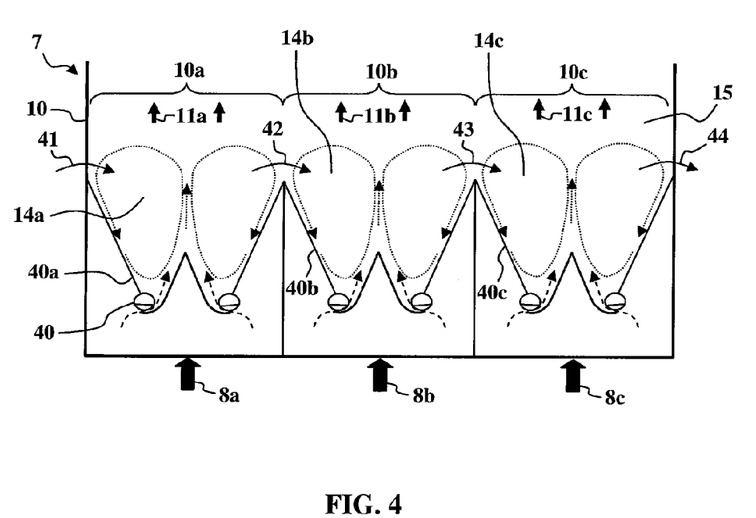
FIG. 4 is a longitudinal cross section schematically illustrating a continuous fluidized bed installation with three successive processing chambers.

In the case of FIG. 4, the process consists in fluidizing the bed with an air stream that passes, not through a bottom grille, but through long lower slits. FIG. 4 illustrates the device in transverse cross section, in which the cavity 10 is divided, for example, into three processing chambers 10a, 10b and 10c each having a respective suspending-air inlet 8a, 8b or 8c, an upper air outlet 11a, 11b or 11c, and one or two lower longitudinal slits such as the slit 40 for passing the air into the fluidized-bed area 14a, 14b or 14c through a lower separation wall 40a, 40b or 40c. The spraying nozzles, not shown, can spray upward or download.

Means are provided for making the granular material transit, for example by gravity, from one compartment to the other as illustrated by the arrows 41, 42, 43 and 44, continuously. In practice, passage of the granular material from one compartment to the other may be achieved by virtue of the orientation of the air flow in the cavity 10.

This principle may be applied to a cavity 10 comprising three processing chambers 10a, 10b and 10c as illustrated in FIG. 4, or to a cavity 10 comprising single comprising a different number of processing chambers.

A description of such a continuous multi-chamber fluidized-bed device may be found, for example, in document US 2006/0 228 661 A1.

Figure 5:
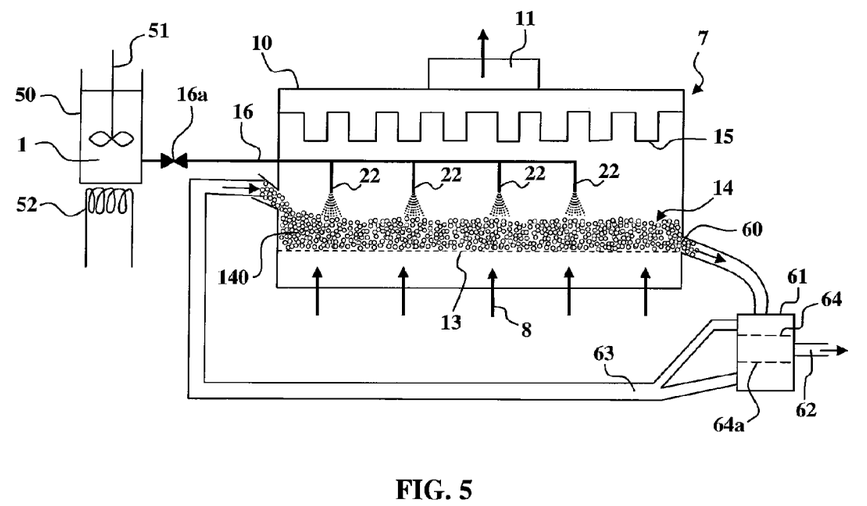
FIG. 5 illustrates the general structure of a continuous production installation according to one embodiment of the present invention.

The device illustrated in FIG. 5, for implementing the process according to the present invention, and comprising a single continuous processing chamber 10, is now considered.

This device includes the cavity 10 with the means for generating and maintaining a fluidized bed 140 in a fluidized-bed area 14, for example: four nozzles 22 connected to the pipe 16, the lower grille 13, the lower air inlet 8, the upper air outlet 11.

The pipe 16 is connected to a mixer 50 provided with stirring means 51 and heating means 52. The heating means 52 are piloted by temperature regulation means to ensure the establishment of a suitable temperature in the mixer 50.

The fluidized-bed device 7 containing a cavity 10 is a device of continuous type. A valve 16a makes it possible to adjust the inlet flow of aqueous solution from the mixer 50.

At the outlet 60 of the cavity 10 is provided a selection device 61 capable of allowing at its outlet 62 passage of the powder grains having a size between a lower limit and an upper limit. The grains that are larger or smaller than the respective limits are recycled into the cavity 10 to continue granulation.

For example, the selection device 61 may comprise two screens 64 and 64a. The two screens allow the small-diameter particles to pass through toward the recycling pipe 63 for them to be recycled. The screen 64 retains the large-diameter particles to return them for recycling, and allows the particles with a suitable average size to pass through, which are retained by the screen 64a to be directed toward the outlet 62.

If FIG. 1 is now considered again, a selection device 61 may also be provided, for example in the form of a central lower outlet not having a screen, but in which is circulated a flow of air in counter-flow 65, which makes a selection by allowing the large-diameter particles to pass through and repelling the finer particles.

The glycinate granulation process was able to be implemented successfully.

The tests made it possible to determine the chemical structure of the samples and to establish the crystalline nature of the powders obtained, by evaluating the heat stability and moisture stability of the samples.

X-ray diffraction was used to establish the chemical structure and the crystalline nature of the products obtained (only crystalline products diffract x-rays).

The moisture content of the powders obtained was determined by halogen desiccation (Mettler-Toledo HR73).

The heat stability was analyzed in an oven at 60° C. for 6 hours in a sealed pill bottle.

The moisture stability was analyzed at 30° C. and 70% humidity, for 6 hours, in an open pill bottle.

Several types of glycinate were thus produced, by selecting the temperature and flow conditions.

The following may be distinguished:
glycinates of type I, whose formula is: $[M(SO_4)(C_2H_5NO_2)]_n$
glycinates of type II, whose formula is: $[M(C_2H_5NO_2)(H_2O)_2(SO_4)]_n$
glycinates of type III, whose formula is: $\{[M(C_2H_5NO_2)(H_2O)_2(SO_4)_2][M(C_2H_5NO_2)(H_2O)_4]\}_n$ in which M is a metal such as iron, zinc, etc.

EXAMPLE 1

Iron Glycinate Via a Continuous Process

The synthesis of iron glycinate may be performed as follows.

A weight mixture of 30.5% water, 56.50% iron II sulfate heptahydrate and 13% glycine is prepared.

The water is heated to 60° C., and the iron II sulfate heptahydrate and the glycine are then introduced into the water in a mixer.

The mixture is stirred and heated until it reaches a temperature of 70° C., for at least 15 minutes.

This solution is then sprayed (by granulation) in a fluidized bed with a bottom-spray system in a Glatt Procell 5 machine (Glatt GmbH, Weimar, Germany).

The flow rate of suspending air in the Glatt Procell 5 machine is set at 150 m³/hour. The product temperature is 59° C. The spraying-air pressure is 2.5 bar. The spraying rate is 20 g/minute. The nozzle diameter is 1.2 mm. The air inlet temperature is 95° C. The air outlet temperature is 50° C.

The product having a satisfactory grain size is collected continuously. Measurement of the moisture content may be performed using an infrared or halogen desiccator, or via thermogravimetry. In the present case, the moisture content is 5.6% (formulation 1).

The analyzed product is crystalline. It diffracts x-rays. It is formed predominantly of anhydrous iron glycinate (type I).

The manufactured sample is entirely heat-stable and moisture-stable. In addition, its very uniform physical appearance, with the virtually total absence of fine particles, gives it excellent flowability and absence of pulverulence.

EXAMPLE 2

Copper Glycinates

The synthesis of copper glycinates may be performed as follows.

A weight mixture of 37.69% water, 48.02% copper sulfate pentahydrate and 14.29% glycine is prepared.

The water is heated to 55° C., and the copper II sulfate pentahydrate and the glycine are then introduced into the water in a mixer.

The mixture is stirred and heated until it reaches a temperature of 70° C., for at least 15 minutes.

This solution is then sprayed (by granulation) in a fluidized bed with a bottom-spray system in a Glatt Procell 5 machine (Glatt GmbH, Weimar, Germany).

The flow rate of suspending air in the Glatt Procell 5 machine is set at 100 m³/hour. The product temperature is 65° C. The spraying-air pressure is 2.5 bar. The spraying rate is 23 g/minute. The nozzle diameter is 1.2 mm. The air inlet temperature is 110° C. The air outlet temperature is 50° C.

The product having a satisfactory grain size is collected continuously. Measurement of the moisture content may be performed using an infrared or halogen desiccator, or via thermogravimetry. In the present case, several moisture contents were tested (table 1).

TABLE 1

Moisture content of formulations F2 to F6

| Sample | Moisture content |
|---|---|
| Copper glycinate (Formulation 2) | 13% |
| Copper glycinate (Formulation 3) | 12% |
| Copper glycinate (Formulation 4) | 9% |
| Copper glycinate (Formulation 5) | 7% |
| Copper glycinate (Formulation 6) | 5% |

All the analyzed products are crystalline: they all diffract x-rays.

The moisture content affects the chemical structure of the copper glycinate (table 2).

TABLE 2

Estimations of the weight proportion of dihydrated (type II) and anhydrous (type I) copper glycinate

| Sample | % CuG dihydrate | % anhydrous CuG |
|---|---|---|
| Formulation 2 | 97.9 | 2.1 |
| Formulation 3 | 96 | 4 |
| Formulation 4 | 86 | 14 |
| Formulation 5 | 75 | 25 |
| Formulation 6 | 57 | 43 |

All the samples tested are entirely heat-stable. In addition, their very uniform physical appearance, with the virtually total absence of fine particles, gives them excellent flowability and absence of pulverulence.

EXAMPLE 3

Zinc Glycinates

The synthesis of zinc glycinates may be performed as follows.

A weight mixture of 57.7% water, 29.9% zinc sulfate monohydrate and 12.5% glycine is prepared.

The water is heated to 55° C., and the zinc sulfate monohydrate and the glycine are then introduced into the water in a mixer.

The mixture is stirred and heated until it reaches a temperature of 70° C., for at least 15 minutes.

This solution is then sprayed (granulation) in a fluidized air bed with a bottom-spray system in a Glatt Procell 5 machine (Glatt GmbH, Weimar, Germany).

The flow rate of suspending air in the Glatt Procell 5 machine is set at 150 m$^3$/hour. The product temperature is 59° C. The spraying-air pressure is 2.5 bar. The spraying rate is 23 g/minute. The nozzle diameter is 1.2 mm. The air inlet temperature is 95° C. The air outlet temperature is 50° C.

The product having a satisfactory grain size is collected continuously. Measurement of the moisture content may be performed using an infrared or halogen desiccator, or via thermogravimetry. In the present case, several moisture contents were tested (table 3).

TABLE 3

| Moisture content of formulations F7 to F9 | |
|---|---|
| Sample | Moisture content |
| Zinc glycinate (Formulation 7) | 2% |
| Zinc glycinate (Formulation 8) | 13% |
| Zinc glycinate (Formulation 9) | 17% |

All the analyzed products are crystalline: they all diffract x-rays.

The zinc glycinate of formulation 7 is formed from anhydrous zinc glycinate (type I).

The zinc glycinate of formulation 8 is formed from zinc glycinate dihydrate (type II).

The zinc glycinate of formulation 9 is formed from zinc glycinate trihydrate (type III).

All the samples tested are entirely heat-stable and moisture-stable. In addition, their very uniform physical appearance, with the virtually total absence of fine particles, gives them excellent flowability and absence of pulverulence.

EXAMPLE 4

Iron Glycinate Via a Batchwise Process

An aqueous solution of iron glycinate is prepared from water, iron II sulfate heptahydrate and glycine as in example 1 above.

This solution is then dried (by granulation) batchwise in a fluidized bed in a Glatt Procell 5 machine, in which the parameters below are applied for processing of the whole batch of material contained in the machine.

The suspending-air flow rate is set at 150 m$^3$/hour. The spraying flow rate is 25 g/minute. The nozzle diameter is 1.2 mm. During the spraying period, the temperature of the product inside the machine is 55° C. The air inlet temperature is 90° C. The air outlet temperature is 46° C. At the end of the spraying step, the product is dried by increasing the temperature of the product until the desired moisture content is obtained. In the present case: 6%. When there is no more spraying of solution in the system, the temperature of the product increases naturally. Without varying the air inlet parameters, it suffices to wait for the moisture content to fall.

The manufactured sample is entirely heat-stable and moisture-stable. In addition, its very uniform physical appearance, with the virtually total absence of fine particles, gives it excellent flowability and absence of pulverulence.

In conclusion, the fluidized-bed technique makes it possible readily to obtain water-soluble crystalline complexes of glycine or other water-soluble amino acids such as valine, threonine, lysine, etc.

According to one aspect, the invention thus provides a crystalline organometallic complex in powder form, in which the powder grains are all larger than about 25 μm in size.

The crystalline structure and the large particle size of such products enable the products to be moisture-stable and heat-stable. They are also entirely free-flowing and free of very small unsuitable particles.

Preferably, for use as feed additives for reared animals, the invention provides a crystalline organometallic complex in powder form, in which the powder grains are between about 100 and 800 μm in size and advantageously between about 200 and 400 μm in size.

In this way, the uniform particle size further promotes the consistency of the properties of successive batches of products, and avoids the presence of excessively large grains, which would be unsuitable for applications in animal feed.

Preferably, the powder grains have a moisture content of less than about 20% and advantageously less than about 6%.

As a result of the manufacturing process, the powder grains have a grain structure derived from a fluidized bed, i.e. they have a compact stratified structure.

The present invention is not limited to the embodiments that have been explicitly described, but includes the diverse variants and generalizations thereof contained in the scope of the claims hereinbelow.

The invention claimed is:

1. Process for producing a crystalline organometallic complex in powder form, comprising the steps of:
    a) preparing an aqueous solution of the organometallic complex,
    b) granulating and drying said solution by spraying in a fluidized bed by circulation of air,
    c) extracting the powder grains from the fluidized bed when they have reached a size greater than a predetermined lower size limit and a moisture content below a predetermined maximum moisture content,
    wherein said predetermined lower size limit is about 25 μm,
    and wherein the predetermined maximum moisture content is between 2% and 20% by weight.

2. Process according to claim 1 wherein, during the step of granulation and drying in a fluidized bed, the temperature and flow rate parameters of the aqueous solution and of the air are chosen so as to obtain, at the end of the step, powder grains having a moisture content below said predetermined maximum moisture content.

3. Process according to claim 1, wherein:
    said solution is granulated and dried continuously by spraying in an air-fluidized bed,
    the temperature and flow rate parameters of the aqueous solution and of the air are continuously adapted so as to obtain in the fluidized bed a moisture content below said predetermined maximum moisture content, the powder grains having a size greater than said predetermined lower size limit are continuously extracted from the fluidized bed.

4. Process according to claim 3 wherein, during a preliminary training step, inlet air, outlet air and inlet aqueous solution flow rates and temperatures are determined, making it possible to produce a flow of outlet powder grains having a moisture content, measured by collecting samples, that is substantially equal to said predetermined maximum moisture content, and said flow rate and temperature values are then maintained throughout the process.

5. Process according to claim 1 wherein:
a batch of material is granulated and dried by spraying said solution in a fluidized-air bed,
after the powder grains in the fluidized bed have reached a size larger than the predetermined lower size limit, the spraying is stopped while continuing maintenance in the fluidized bed to perform drying until a moisture content below the predetermined maximum moisture content is reached,
the mass of powder grains having this size and this moisture content is extracted.

6. Process according to claim 1 wherein, during the step of preparation of the organometallic complex, the mixture temperature is maintained in the range from about 55° C. to 80° C.

7. Process according to claim 1 wherein, during step a), water, amino acid and a water-soluble metal salt are mixed together with heating in a mixer until a temperature of 80° C. is reached, for at least 15 minutes.

8. Process according to claim 7 wherein the water is introduced and is heated first in the mixer, then the amino acid and the metal salt are added, and the mixture is stirred and heated until a temperature of 80° C. is reached, for at least 15 minutes.

9. Process according to claim 1 wherein, to prepare an anhydrous iron glycinate, glycine is used as amino acid, iron II sulfate heptahydrate is used as metal salt, and the moisture content is about 6%.

10. Process according to claim 1 wherein, to prepare copper glycinate dihydrate, glycine is used as amino acid, copper sulfate pentahydrate is used as metal salt, and the moisture content is about 13%.

11. Process according to claim 1 wherein, to prepare anhydrous zinc glycinate, glycine is used as amino acid, zinc sulfate monohydrate is used as metal salt, and the moisture content is about 2%.

12. Process according to claim 1 wherein, to prepare zinc glycinate dihydrate, glycine is used as amino acid, zinc sulfate monohydrate is used as metal salt, and the moisture content is about 13%.

13. Process according to claim 1 wherein, to prepare zinc glycinate trihydrate, glycine is used as amino acid, zinc sulfate monohydrate is used as metal salt, and the moisture content is about 17%.

14. Process for producing a crystalline organometallic complex in powder form, comprising the steps of:
a) preparing an aqueous solution of the organometallic complex,
b) granulating and drying said solution by spraying in a fluidized bed by circulation of air,
c) extracting the powder grains from the fluidized bed when they have reached a size greater than a predetermined lower size limit and a moisture content below a predetermined maximum moisture content,
wherein said predetermined lower size limit is about 80 μm,
and wherein the predetermined maximum moisture content is between 2% and 20% by weight.

* * * * *